(12) United States Patent
Park et al.

(10) Patent No.: US 7,684,854 B2
(45) Date of Patent: Mar. 23, 2010

(54) APPARATUS AND METHOD FOR MEASURING ELECTRIC NON-CONTACT ELECTROCARDIOGRAM IN EVERYDAY LIFE

(75) Inventors: Kwang-Suk Park, Seoul (KR); Yong-Kyu Lim, Seoul (KR); Ko-Keun Kim, Ansan-si (KR)

(73) Assignee: Seoul National University Industry Foundation, Seoul (KR)

( * ) Notice: Subject to any disclaimer, the term of this patent is extended or adjusted under 35 U.S.C. 154(b) by 488 days.

(21) Appl. No.: 11/631,704

(22) PCT Filed: Aug. 31, 2005

(86) PCT No.: PCT/KR2005/002885

§ 371 (c)(1),
(2), (4) Date: Jan. 5, 2007

(87) PCT Pub. No.: WO2006/031025

PCT Pub. Date: Mar. 23, 2006

(65) Prior Publication Data

US 2007/0255152 A1    Nov. 1, 2007

(30) Foreign Application Priority Data

Aug. 31, 2004  (KR) .................... 10-2004-0068943

(51) Int. Cl.
*A61B 5/0444* (2006.01)

(52) U.S. Cl. ...................... 600/509; 600/382

(58) Field of Classification Search ......... 600/374–393, 600/508, 509
See application file for complete search history.

(56) References Cited

U.S. PATENT DOCUMENTS

| 3,731,672 | A  | * | 5/1973 | McIntosh ............... 600/516 |
| 5,503,158 | A  | * | 4/1996 | Coppock et al. ......... 600/508 |
| 6,745,062 | B1 | * | 6/2004 | Finneran et al. ......... 600/393 |
| 6,961,601 | B2 | * | 11/2005 | Matthews et al. ........ 600/372 |
| 7,245,956 | B2 | * | 7/2007 | Matthews et al. ........ 600/382 |

OTHER PUBLICATIONS

"Monitoring of Electrocardiograms in Bed Without Utilizing Body Surface Electrodes", By Ishijima, published by IEEE Transactions on Biomedical Engineering, vol. 40, No. 6, Jun. 1993.

* cited by examiner

*Primary Examiner*—Scott M Getzow
(74) *Attorney, Agent, or Firm*—Bachman & LaPointe, P.C.

(57) ABSTRACT

The present invention relates generally to an electric non-contact apparatus and method for taking electrocardiograms and, more particularly, to an electric non-contact apparatus and method for taking electrocardiograms, in which an examinee can have an electrocardiogram taken in a comfortable position because the apparatus and method are applied to a chair, a bed or a vehicle seat, which are widely used in daily life, and in which the examinee can unnoticeably have an electrocardiogram taken without being conscious of the taking of the electrocardiogram because the taking of the electrocardiogram is performed on the body of a human wearing clothes without directly contacting the body.

9 Claims, 10 Drawing Sheets

APPARATUS AND METHOD FOR MEASURING ELECTRIC NON-CONTACT ELECTROCARDIOGRAM IN EVERYDAY LIFE

TECHNICAL FIELD

The present invention relates generally to an electric non-contact apparatus and method for taking electrocardiograms and, more particularly, to an electric non-contact apparatus and method for taking electrocardiograms, which are applied to a chair, a bed or a vehicle seat widely used in daily life, so that an examinee can have an electrocardiogram taken in a comfortable position, and which perform the taking of the electrocardiogram on the body of a human wearing clothes without directly contacting the body, so that the examinee can unnoticeably have an electrocardiogram taken without being conscious of the taking of the electrocardiogram.

BACKGROUND ART

An ECG refers to a record of action current attributable to the contraction of the heart using a curve, and is an abbreviation for an electrocardiogram.

Since the excitation of the heart muscle first occurs in the sinus venosus and proceeds toward the auricle and the cardiac ventricle, the action current of the heart is depicted on a graph when the excitation is introduced from two arbitrary points to an ammeter (electrocardiograph).

A diagram, in which action potentials, which are generated by electric excitation that occurs when the heart muscle contracts, are transferred to the surface of a human body and waveforms caused by the current are depicted, is an ECG. This ECG is very important in the diagnosis of heart diseases.

In this diagram, in the case where the indicator needle of an ammeter draws an upward curve when the base portion of the heart is excited and becomes electrically negative with respect to the tip portion, the portions projected from an equipotential line are denoted by P, Q, R, S, T and U waves, according to the W. Ainthoben's nomenclature.

In order to obtain an ECG for the diagnosis of heart diseases, ECG methods using standard limb induction based on both hands (first induction: Lead I), a right hand and a left foot (second induction: Lead II), and a left hand and a left foot (third induction: Lead III) are used, as illustrated in FIG. 1. In addition, there are ECG methods using unipolar induction and chest induction.

The taking of ECGs is widely used in the diagnosis of coronary diseases, such as angina pectoris and myocardial infarction, arrhythmia, and electrolyte disorders, in the examination and determination of whether a disorder of the heart exists during an operation, and is important in the diagnosis of heart diseases.

Such an ECG is based on some biosignal, other than a biosignal related to an electromyogram, a brain wave, or a bio-impedance signal. The biosignal related to the ECG is a signal that is fundamental to the diagnosis of the health condition of an examinee and that uses a non-invasive method. The biosignal related to an ECG is widely used in clinical practice, along with a respiration signal.

In a medical field requiring the measurement of biopotentials, such as those for an ECG, an electromyogram and an electroencephalogram, to perform appropriate treatment, a method of transmitting electric signals from a body to an external device and making a diagnosis has been recently commercialized.

A conventional apparatus for taking ECGs, as illustrated in FIG. 2, includes a conductive fiber electrode 100 and an ECG amplifier 200. The conductive fiber electrode 100 includes three conductive fiber patches 101 and 101' that are attached to the mattress of a bed.

The conductive fiber electrode 100 is formed by coating a polyester filament with copper and nickel, and is configured to conduct electricity.

For an examinee to have an ECG taken, the examinee wears clothes, including an upper garment allowing the chest or shoulders to be exposed to the outside, and knee pants, and lays himself or herself on a bed so that his or her back or shoulders come into contact with the two conductive fiber patches 101 provided on one side of the bed and his or her feet come into contact with the one conductive fiber patch 101'.

After the examinee's parts have come into contact with the conductive fiber patches 101 and 101' as described above, the examinee's ECG is taken by the ECG method using Lead I, II or III through an ECG amplifier, as described in conjunction with FIG. 1.

A conventional apparatus for taking ECGs in an unnoticeable and unrestrictive manner is disclosed in Ishijima's thesis: Masa Ishijima, 'Monitoring of ECGs in Bed Without Utilizing Body Surface Electrodes', IEEE Transactions on Biomedical Engineering, Vol 40, No 6, June 1993, p 593-594. This apparatus is disadvantageous in that the surface of a body must be brought into contact with electrodes exposed on a bed because an ECG is taken directly on the surface of the examinee's body, so that the examinee must put on and take off clothes to have an ECG taken, which may be unpleasant for the examinee.

Furthermore, the conventional ECG apparatus and method have limitations in that it is not easy to repeatedly have an ECG taken at home using the ECG apparatus and method used in medical institutions, and it is inconvenient for unskilled persons to use the ECG apparatus. Moreover, the conventional ECG apparatus and method has a problem in that, when an examinee has an ECG taken using the conventional ECG apparatus and method, the examinee is aware that an ECG is being taken, so that it is difficult to obtain accurate ECG values.

DISCLOSURE

[Technical Problem]

Accordingly, the present invention has been made keeping in mind the above problems occurring in the prior art, and an object of the present invention is to provide an electric non-contact apparatus and method for taking electrocardiograms, which are applied to a chair, a bed or a vehicle seat widely used in daily life, so that an examinee can have an electrocardiogram taken in a comfortable position, which perform the taking of the electrocardiogram on the body of a human wearing clothes without directly contacting the body, so that the examinee can unnoticeably have an electrocardiogram taken without being conscious of the taking of the electrocardiogram, and which do not require work of bringing the ECG apparatus and electrodes into contact with the body or work of attaching the ECG apparatus and the electrodes thereto, so that unskilled persons can use the ECG apparatus and method, thereby improving the convenience of use.

[Technical Solution]

In order to accomplish the above object, the present invention provides an apparatus for taking ECGs, the apparatus being attached to a human body, including one or more amplifier-attached electrodes installed adjacent to appropriate locations of clothes without directly contacting a body; one or more filter and amplifier units connected to first sides of the amplifier-attached electrodes and configured to filter out external noise and amplify filtered signals; one or more A/D converters connected to first sides of the filter and amplifier units; a digital signal processing unit provided to first sides of the A/D converter and configured to transmit a taken ECG to a display and a post-processing device; and a ground plate installed adjacent to an appropriate location on the clothes without directly contacting the body.

Preferably, each of the amplifier-attached electrodes includes an electrode face provided on one side of the amplifier-attached electrode, a preamplifier for amplifying and impedance-converting a biosignal input through the electrode face, and a shield provided around the preamplifier.

In the apparatus, each of the filter and amplifier units includes a high pass filter circuit for filtering out variation of offset accompanying the biosignal input to the preamplifier of the amplifier-attached electrode in displacement current form, a band stop filter circuit for filtering out 60 Hz band common-mode noise from a biosignal input through the high pass filter circuit, an amplification circuit for amplifying a biosignal, which is input through the band stop filter circuit, at a predetermined amplification ratio, and a low pass filter circuit for extracting a low band signal of 100 Hz or lower frequency from a biosignal input through the amplification circuit and outputting the lower band signal as an analog signal.

Meanwhile, each of the A/D converters is configured to convert the biosignal-based analog signal, which is input through the filter and amplifier unit, into a digital signal.

The digital signal processing unit includes a subtractor for obtaining a difference between the digitized biosignals input through the A/D converters, and a subtraction filter for filtering out noise, which is generated during the subtraction, from the digital signals input through the subtractor.

When the electric non-contact ECG apparatus is applied to a chair, the amplifier-attached electrodes are installed on appropriate sides of a backrest part of the chair on which both shoulders of an examinee are placed, and the ground plate is installed at a predetermined location on a seat of the chair on which buttocks of the examinee are placed.

Preferably, when the electric non-contact ECG apparatus is applied to a chair, the amplifier-attached electrodes are installed on appropriate sides of a seat of the chair where both thighs of an examinee are placed, and the ground plate is installed at a predetermined location on a backrest part of the chair on which both shoulders of the examinee are placed.

When the electric non-contact ECG apparatus is applied to a bed, the amplifier-attached electrodes are installed on a first side of an upper surface of a mattress of the bed on which both shoulders of an examinee are placed, and the ground plate is installed on a second side of the upper surface of the mattress of the bed on which buttocks of the examinee are placed.

Alternatively, when the electric non-contact ECG apparatus is applied to a bed, the amplifier-attached electrodes are installed on a first side of an upper surface of a mattress of the bed on which thighs of an examinee are placed, and the ground plate is installed on a second side of the upper surface of the mattress of the bed on which both shoulders of the examinee are placed.

When the electric non-contact ECG apparatus is applied to a driver's seat of a vehicle, the amplifier-attached electrodes are installed on appropriate sides of a steering wheel, which is provided in front of the driver's chair and is used to steer the vehicle, to enable direct contact, and the ground plate is installed at a predetermined location on a seat part of the driver's seat.

Preferably, when the electric non-contact ECG apparatus is applied to a driver's seat of a vehicle, the amplifier-attached electrodes are installed on appropriate sides of a seat part of the driver's seat where thighs of a driver are placed, and the ground plate is installed on a steering wheel, which is provided in front of the driver's chair and is used to steer the vehicle, to enable direct contact.

Meanwhile, the present invention provides a method of taking ECGs of examinees based on an ECG apparatus, the ECG apparatus having one or more amplifier-attached electrodes, one or more filter and amplifier units, one or more A/D converters, a digital signal processing unit and a ground plate, including the step at which biosignals, which are generated in an examiner's body, are input to the amplifier-attached electrodes across worn clothes via displacement current; the step at which the input biosignals are amplified and impedance-converted by the amplifier-attached electrodes; the step at which the biosignals, which are converted by the amplifier-attached electrodes, are input to the filter and amplifier units; the step at which the input biosignals are filtered and amplified by the filter and amplifier units; the step at which biosignal-based analog signals, which are output from the filter and amplifier units, are input to the A/D converters; the step at which the biosignal-based analog signals are converted into digital signals by the A/D converters; the step at which the digital signals, which are obtained by the A/D converters, are input to the digital signal processing unit; and the step at which an ECG, on which subtraction and filtering are performed by the digital signal processing unit, is displayed on a display.

Preferably, the biosignals input to the amplifier-attached electrodes are detected by electrode faces and the biosignals are amplified and impedance-converted by preamplifiers.

Variation of offset is eliminated and filtered out from the biosignals, which are input to the amplifier-attached electrodes, by high pass filter circuits, 60 Hz band common-mode noise passed through the high pass filter circuit is eliminated and filtered out by a low pass filter circuit, the biosignals passed through the low pass filter circuit are amplified at a predetermined amplification ratio by an amplification circuit, and the amplified biosignals amplified by the amplification circuit are output as analog signals in a low signal band.

The digital signals input to the digital signal processing unit are subtracted by the subtractor, and noise, which is generated during the subtraction through the subtractor, is eliminated by a subtraction filter.

Meanwhile, the ground plate eliminates common-mode noise of the body in such a way as to detect the common-mode noise by performing subtraction and addition on the signals input from the amplifier-attached electrodes, and connect to the amplifier-attached electrodes in a negative feedback fashion.

[Advantageous Effects]

The present invention is advantageous in that the present invention is applied to a chair, a bed or a vehicle seat widely used in daily life, so that an examinee can have an electrocardiogram taken in a comfortable position, which performs the taking of the electrocardiogram on the body of a human wearing clothes without directly contacting the body, so that the examinee can unnoticeably have an electrocardiogram taken without being conscious of the taking of the electrocardiogram, thus obtaining a heart rate that can be used as a parameter useful to analyze physical and metal activities, and which does not require work of bringing the ECG apparatus and electrodes into contact with the body or work of attaching the ECG apparatus and the electrodes thereto, so that unskilled persons can use the ECG apparatus and method, thereby improving the convenience of use.

Figure 1:
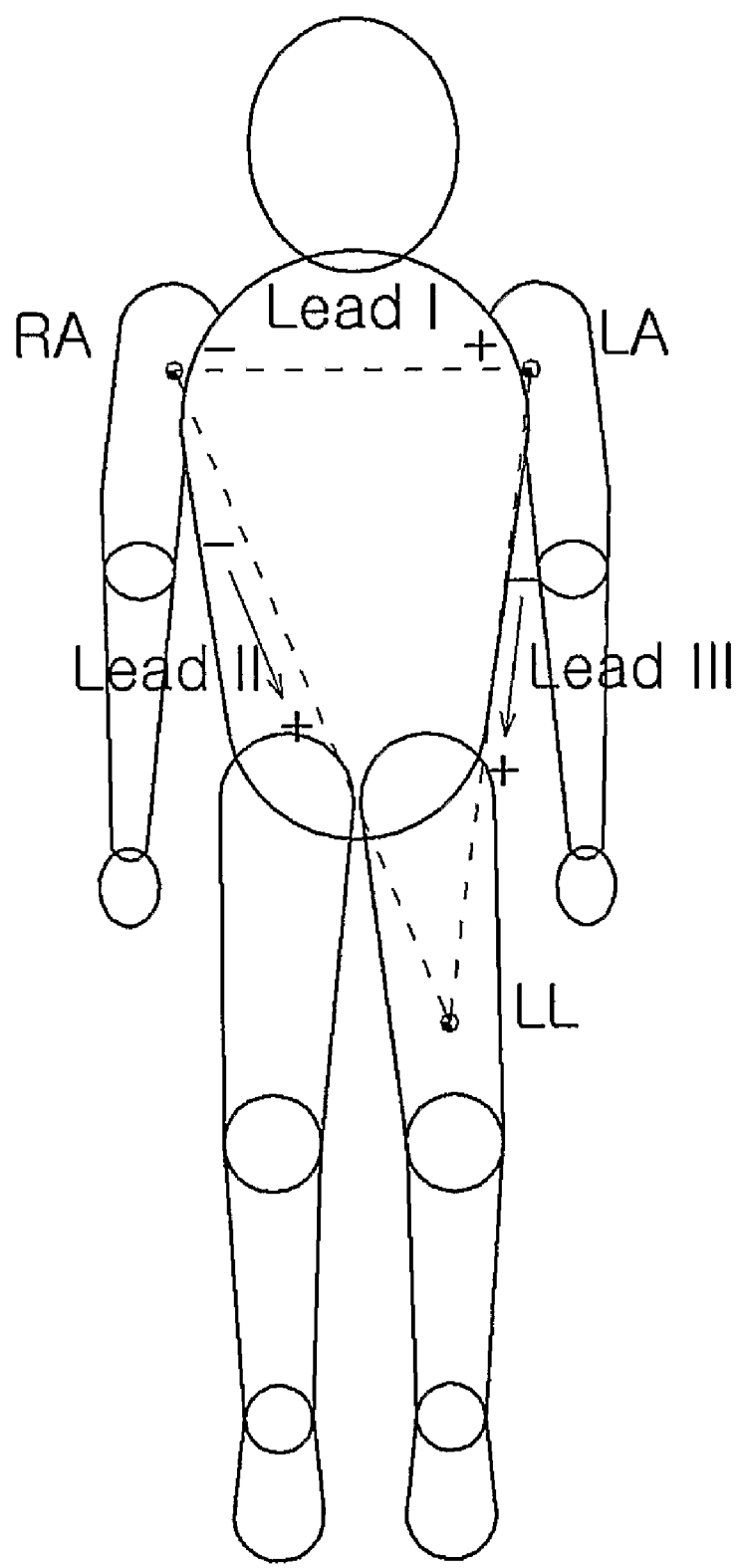
FIG. 1 is a diagram schematically illustrating a conventional method of taking ECGs.
Figure 2:
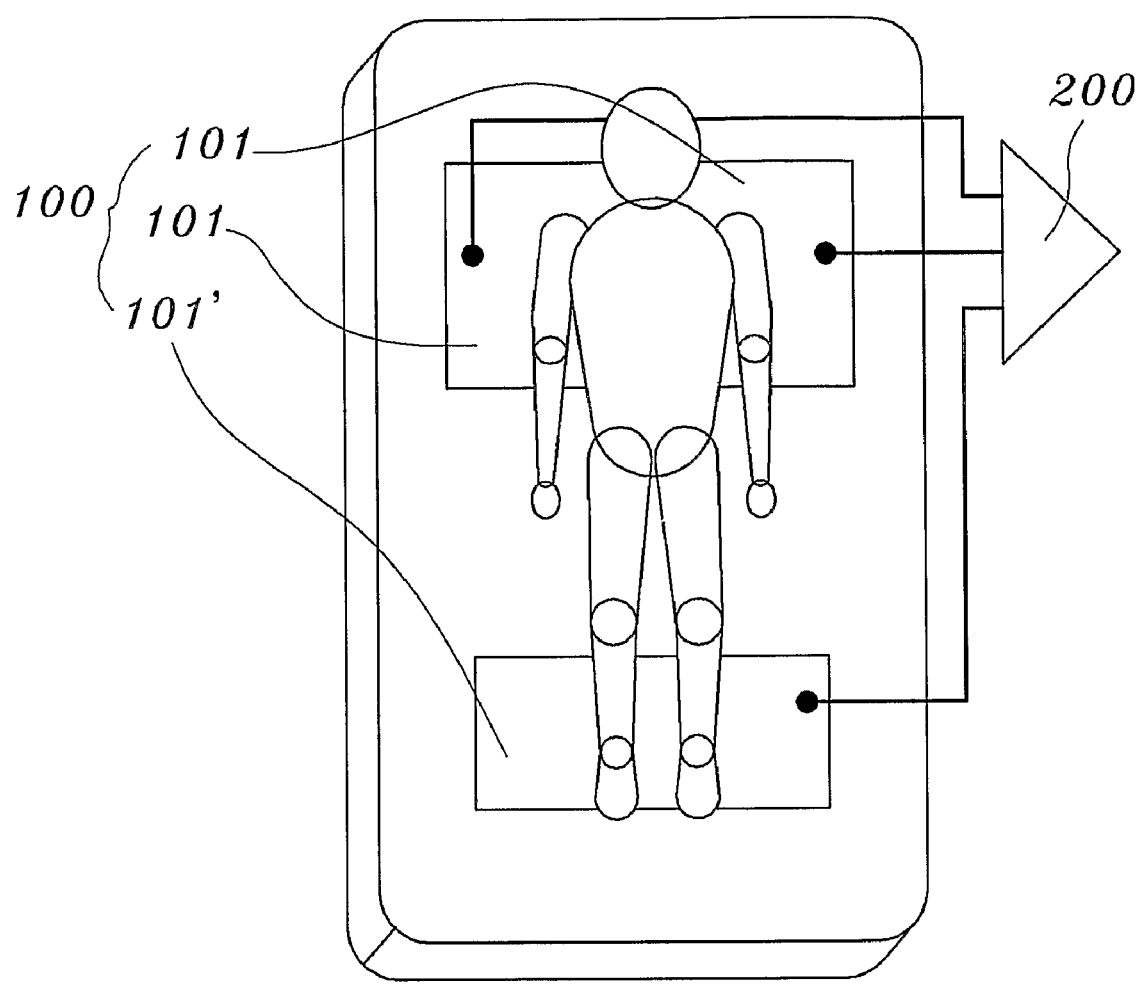
FIG. 2 is a diagram illustrating an example of the use of a conventional apparatus for taking ECGs.

DESCRIPTION OF REFERENCE CHARACTERS
OF IMPORTANT ELEMENTS

1: non-contact ECG apparatus,
3: body,
5: clothes,
10: amplifier-attached electrode,
11: electrode face,
13: pre-amplifier,
15: shield,
30: filter and amplifier unit,
31: high pass filter circuit,
33: pass stop filter circuit,
35: amplification circuit,
37: low pass filter circuit,
50: A/D converter,
70: digital signal processing unit,
71: subtractor,
73: subtraction filter,
80: ground plate,
91: chair,
93: bed,
95: driver's seat,
96: steering wheel,
97: backrest part,
99: seat part

[Best Mode]

Preferred embodiments of the present invention are described in detail below. However, the following embodiments are provided for illustrative purposes, and the present invention is not limited to the following embodiments.

Figure 3:
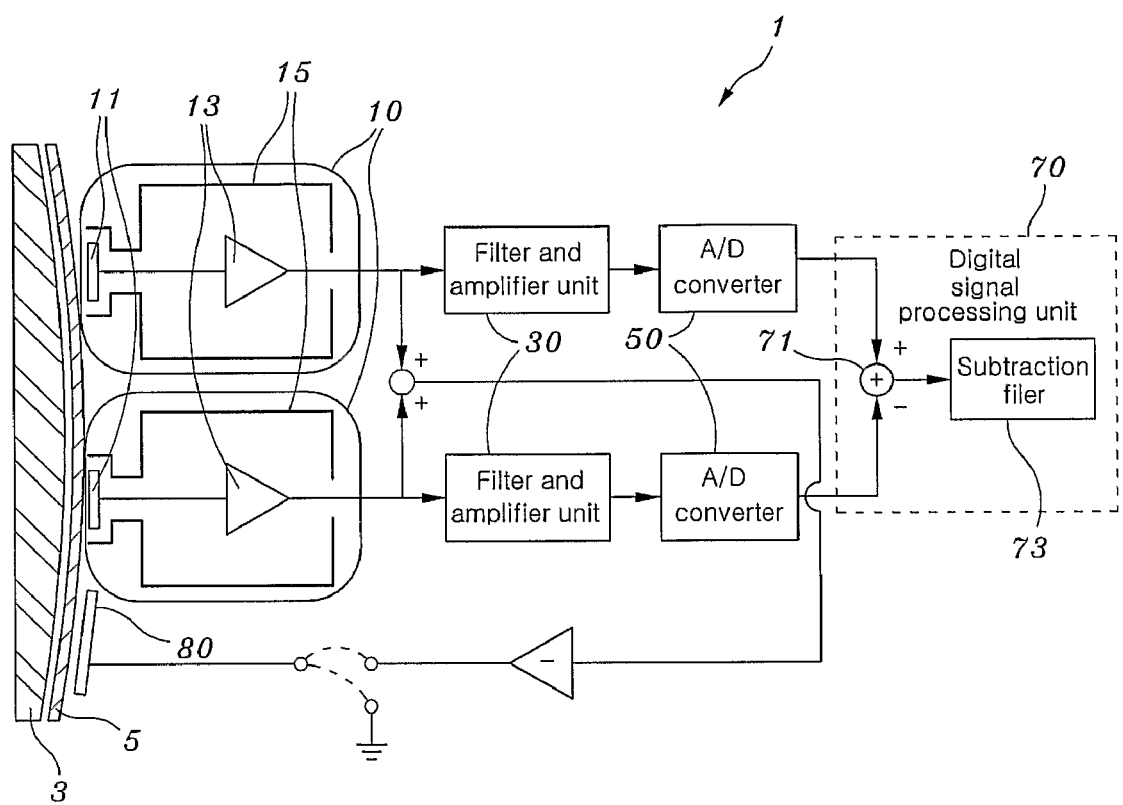
FIG. 3 is a block diagram schematically illustrating an electric non-contact apparatus for taking ECGs, according to the present invention.
Figure 4:
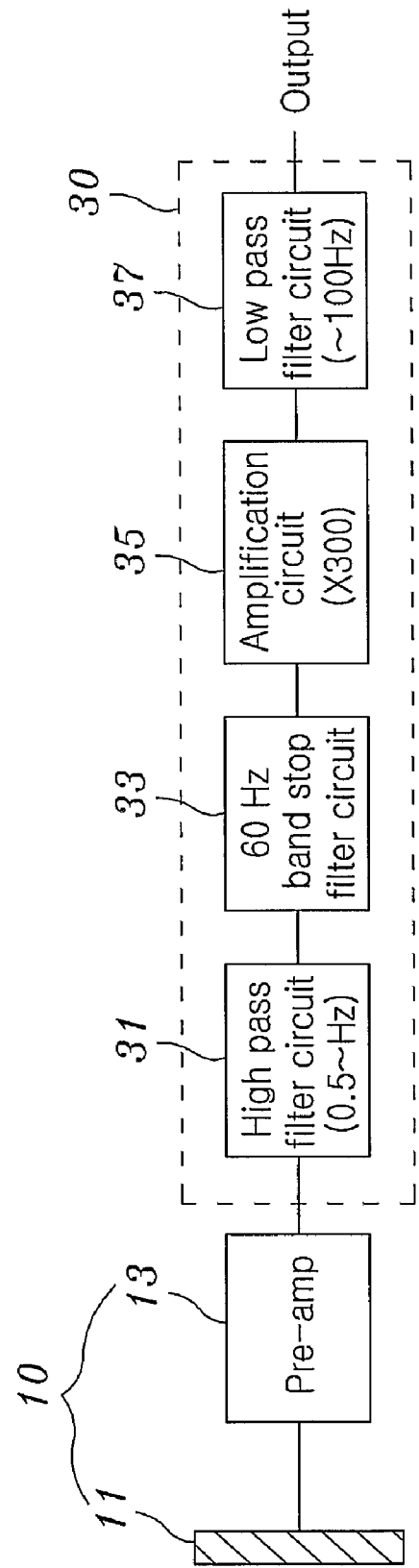
FIG. 4 is a diagram illustrating the filter and amplification unit of the electric non-contact ECG apparatus.
Figure 5:
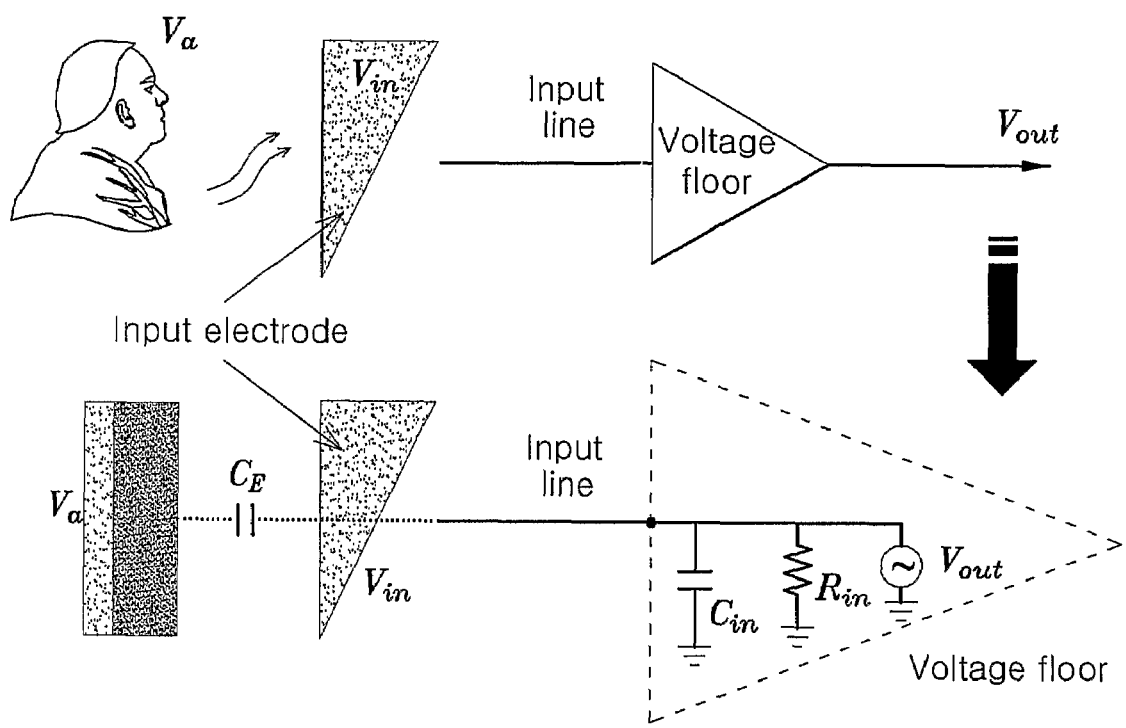
FIG. 5 is a diagram illustrating input impedance depending on the gain value of the electric non-contact apparatus for taking ECGs.
Figure 6:
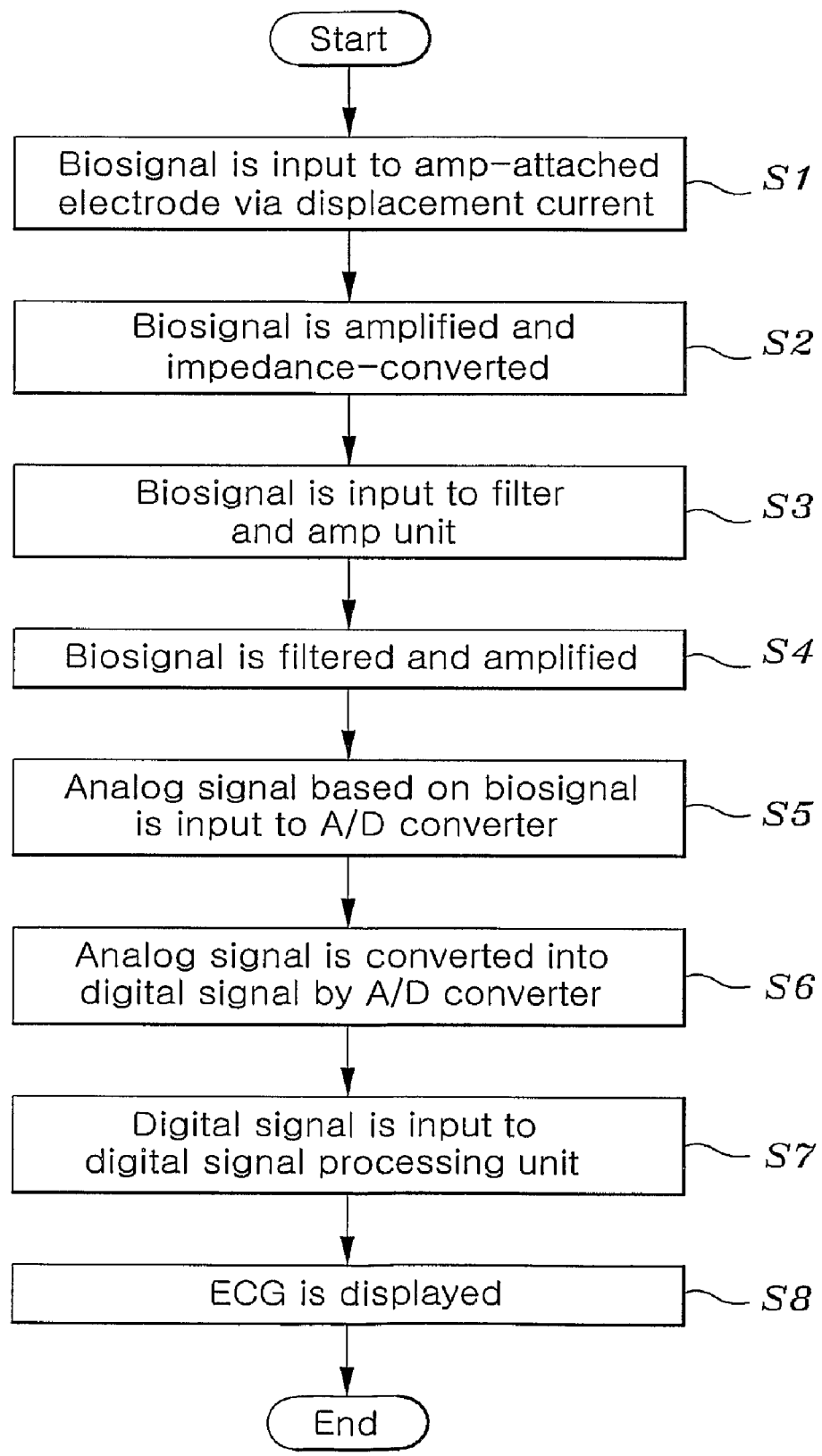
FIG. 6 is an electric non-contact method of measuring ECGs based on the electric non-contact apparatus, according to the present invention.

FIG. 3 is a block diagram schematically illustrating an electric non-contact apparatus for taking ECGs, according to the present invention. FIG. 4 is a diagram illustrating the filter and amplification unit of the electric non-contact ECG apparatus. FIG. 5 is a diagram illustrating input impedance depending on the gain value of the electric non-contact apparatus for taking ECGs. FIG. 6 is an electric non-contact method of measuring ECGs based on the electric non-contact apparatus, according to the present invention.

As illustrated in the drawings, the electric non-contact apparatus for measuring an ECG includes an amplifier-attached electrode 10, a filter and amplifier unit 30, an A/D converter 50, a digital signal processing unit 70, and a ground plate 80.

The amplifier-attached electrode 10 has an electrode face 11 at one side thereof, and includes a preamplifier 13 that amplifies a minute biosignal, which is input via displacement current without direct physical contact, and converts the signal into voltage. The preamplifier 13 is configured to be shielded by a shield 15. At least one amplifier-attached electrode 10 is provided.

Meanwhile, in a system that does not come into electrical contact with the surface of a body, the measurement of bio-potential is achieved using displacement current. The displacement current is used for a method of transferring an electric signal between the skin of a body and an electrode face. The term "displacement current" refers to current generated while voltage across electrodes, which has a non-conductive material, such as clothes, bedclothes, or leather, therebetween, varies, For example, when a capacitor is discharged, charges located on the upper surface of an electrode plate flow through an external conducting wire in conduction current form and, at the same time, the density of electric force lines varies between the capacitor and the electrode plate, thus forming displacement current. As a result, a single electric circuit is formed throughout the system, and an electric field is generated by the current and propagates through the space in electromagnetic wave form.

In the present invention, a biosignal generated on the surface of a body 3 is input to the amplifier-attached electrode 10 via displacement current, a signal generated by amplification and impedance variation is measured, and high input impedance is generated on the amplifier-attached electrode 10 so as to convert the measured minute biosignal into voltage having a high gain value.

The filter and amplifier unit 30 is configured to be provided on one side of the amplifier-attached electrode 10 and to be connected to the preamplifier 13 of the amplifier-attached electrode 10, so that a generated biosignal is converted into voltage based on an ECG detected by the amplifier-attached electrode 10.

A high pass filter circuit 31 for preventing a phenomenon in which the base line of a biosignal, having passed through the preamplifier 13, fluctuates, and eliminating and filtering out the variation of offset accompanying the biosignal at the time of converting the biosignal into voltage, a band stop filter circuit 33 for eliminating and filtering out 60 Hz band common-mode noise that is the impedance voltage of a human body and is included in the displacement current based on the ECG signal having passed through the high pass filter circuit 31, an amplification circuit 35 for amplifying the minute common-mode noise free biosignal at a predetermined amplification ratio, and a low pass filter circuit 37 for outputting an analog signal in a low signal band lower than 50 Hz after the amplification using the amplification circuit 35 has been performed.

The A/D converter 50 is provided on one side of the filter and amplifier unit 30, and converts the analog signal of the biosignal, which is output through the filter and amplifier unit 30 and based on the ECG, into a digital signal.

The digital signal processing unit 70 is provided to first sides of the A/D converters 50, and includes a subtractor 71 for subtracting the biosignals, which are measured by the amplifier-attached electrodes 10 and are based on the ECG, from each other and a subtraction filter 73 for eliminating noise, which is generated during the subtraction, from the digital signals input through the subtractor 71.

A ground plate 80 is provided on one side of the digital signal processing unit 70, and is disposed adjacent to the clothes of an examinee when the electric non-contact ECG apparatus 1 according to the present invention is applied to a human body.

The ground plate 80 is configured based on a method of directly connecting to a ground or a method of detecting a common-mode signal by adding signals, which are output from the amplifier-attached electrodes 10, to each other, and then connecting the common-mode signal to a ground at an appropriate gain in a negative feedback manner. The entire system for the method of connecting to the ground in a negative feedback manner is more complicated. The latter method is more effective in eliminating common-mode noise.

That is, the method of connecting to the ground in a negative feedback manner amplifies common-mode noise, which is detected by adding the output signals of the two electrodes to each other, using an amplifier having a negative gain and then transfers the common-mode noise to the human body through the ground plate 80, so that the potential of the human body is pulled down contrary to common-mode noise, thereby reducing the magnitude of common-mode noise detected by the electrode. Accordingly, the method of connecting to the ground in a negative feedback manner can eliminate common-mode noise more effectively than the method of directly connecting to the ground.

Meanwhile, when the value $V_{in}$ of the biosignal input to the preamplifier 13 of the amplifier-attached electrode 10 is equal to the value $V_{out}$ of the output biosignal, the gain value of the output biosignal can be represented by $V_{out}/Va=(jwRinCE)/(1+jwRin(C_{in}+CE))$. For the gain value to increase, $C_{in}$ (the amount of total input to the amplifier) must be significantly smaller than CE (capacitance between the electrode and the human body), so that a system having a high input impedance is required. In this case, Rin refers to the total parallel input resistance of the amplifier, and $V_{out}/V_{in}$ is reduced in proportion to Cin.

For this purpose, in the present invention, the input terminal of the system is constructed using an operational amplifier 124 having sufficient input impedance. The operational amplifier 124 is a semiconductor Integrated Circuit (IC) amplifier having low noise, low bias current and high input impedance.

Meanwhile, the electrode face 11 and an electric path extending from the electrode face 11 to the preamplifier 13 maintains significantly high impedance with respect to a ground, so that they are not affected much by external noise. In order to reduce external input noise by minimizing a high impedance portion extending from the electrode face 11 to the amplification circuit 35, the amplifier-attached electrode 10, in which the preamplifier 13 is attached to the electrode face 11, is employed.

The electric non-contact method of measuring an ECG using the electric non-contact apparatus for measuring an ECG according to the present invention is described below with reference to FIG. 5.

First, one or more amplifier-attached electrodes 10 are respectively located adjacent to either side of the thigh of an examinee wearing clothes 5 on the body 3, and the ground plate 80 is located adjacent to the back or shoulders of the examinee.

As described above, at least one amplifier-attached electrode 10 and the ground plate 80 are located adjacent to the specific portions of the body 3 wearing the clothes 5, and conditions for measuring the ECG of the examinee are set, so that a biosignal generated in the body 3 of the examinee can be input to the amplifier-attached electrode 10 in displacement current form at step S1.

At this time, the minute biosignal of the body 3, which is input to the electrode face 11 of the amplifier-attached electrode 10 through the clothes 5, is amplified and impedance-converted at step S2, and the biosignal input to the amplifier-attached electrode 10 and converted is input to the filter and amplifier unit 30 at step S3.

At this time, high impedance is applied to the amplifier-attached electrode 10 so as to convert the minute biosignal generated in the body 3 into voltage having a high gain value voltage.

Meanwhile, the amplifier-attached electrode 10 functions as a kind of sensor for detecting the potential of the skin of the body 3. For this purpose, the amplifier-attached electrode 10 is manufactured by coating one surface of a Printed Circuit Board (PCB) with copper and then plating the PCB with gold.

Assuming that the thickness of the clothes 5 is 1 mm and the specific inductive capacity of the clothes 5 is 2, the capacitance between the amplifier-attached electrode 10 and the human body can be expected to be about 30 pF, and the impedance can be expected to be 0.25 G ohm at 20 Hz.

Meanwhile, the preamplifier 13, which is provided in the amplifier-attached electrode 10, functions to convert the biosignal, which is generated depending on the ECG detected by the amplifier-attached electrode 10, into voltage that can be easily used in the filter and amplifier unit 30. For this purpose, the operational amplifier 124 is used in the preamplifier 13, and the operational amplifier 124 has an input resistance of 1013, an input capacitance of 1 pF and an impedance of about 8 G at 20 Hz.

After the biosignal output from the amplifier-attached electrode 10 having the above-described construction has been input to the filter and amplifier unit 30, the biosignal is filtered and amplified at step S4. The filtered and amplified biosignal is converted into an analog signal and is input to the A/D converter 50 at step S5.

The phenomenon in which the base line of the biosignal fluctuates and the variation in offset are eliminated and filtered out while the biosignal passes through the high pass filter circuit 31 of the filter and amplifier unit 30, the 60 Hz band common-mode noise is eliminated and filtered out while the biosignal passes through the band stop filter circuit 33, the common-mode noise free minute biosignal is amplified by the amplification circuit 35 at a predetermined amplification ratio, and the biosignal amplified by the amplification circuit 35 passes through the low pass filter circuit 37, is output from the low pass filter circuit 37 as an analog signal, and is input to the digital signal processing unit 70.

Meanwhile, the high pass filter circuit 31 is formed of a fourth order Sallen-Key high pass filter so as to eliminate and filter out the phenomenon in which the base line of the biosignal passed through the preamplifier 13 fluctuates, and the variation in offset.

In the signal passed through the amplification circuit 35, a signal, having frequencies lower than 50 Hz and corresponding to the ECG, exists, and signals, having a band higher than 50 Hz, may be considered noise. Since the analog signal output from the low pass filter circuit 37 must be converted into the digital signal, the low pass filter circuit 37 must be configured to pass signals of frequencies lower than 100 Hz, which is double that of the band including the ECG, so as to preventing alising in which frequencies overlap each other. For this purpose, the low pass filter circuit 37 is formed of a fourth order Sallen-Key low pass filter, that is, a kind of active filter circuit.

The analog signal output through the filter and amplifier unit 30 is converted into a digital signal by the A/D converter 50 at step S6.

The digital signal output through the A/D converter 50 is input to the digital signal processing unit 70 at step S7, subtraction is performed on the digital signal by the subtractor 71, noise, which is generated during the subtraction process, is eliminated and output by the subtraction filter 73, and the output ECG is displayed on a display at step S8.

Figure 7:
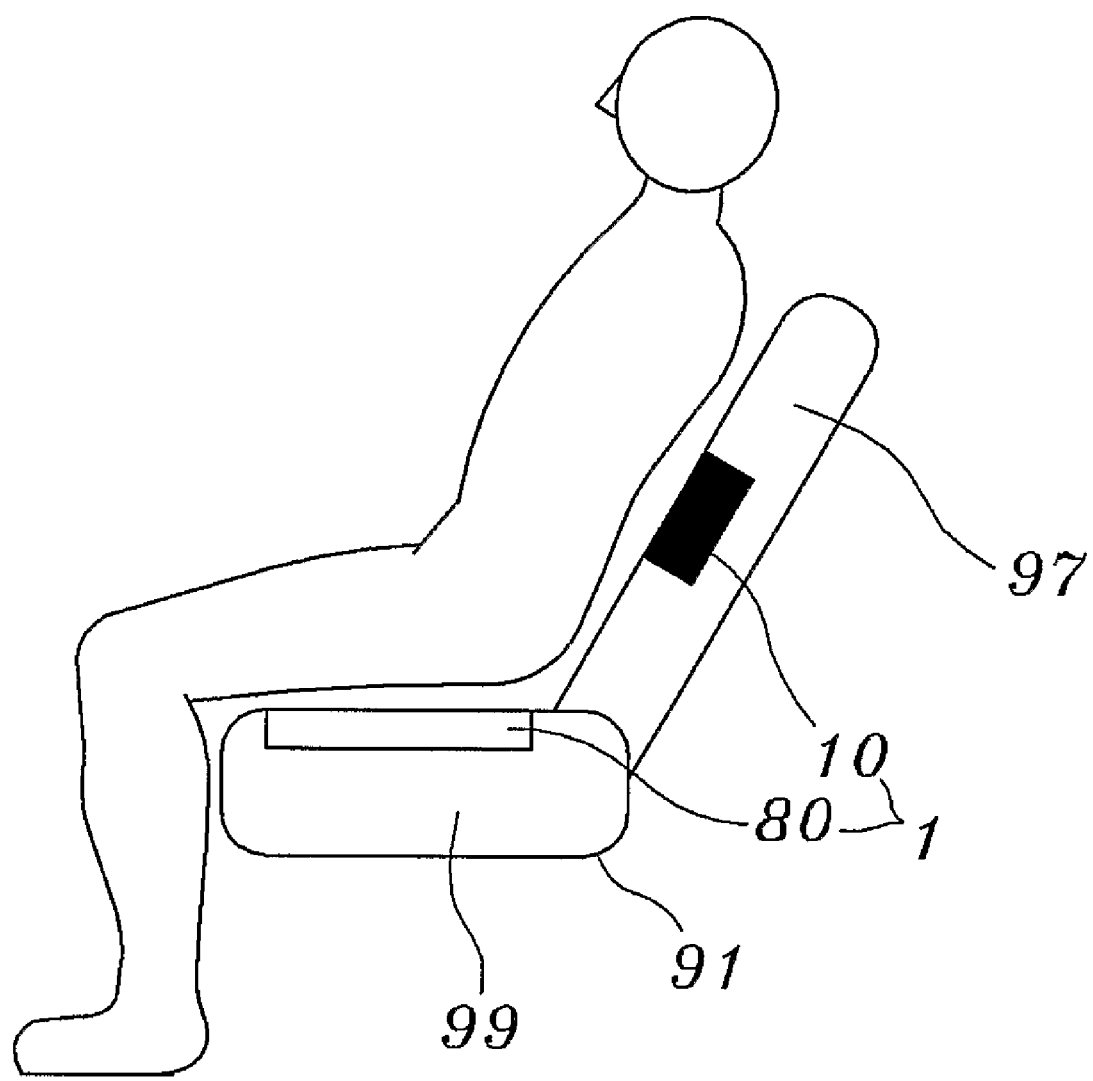
FIG. 7 is a diagram illustrating an electric non-contact apparatus for taking ECGs according to a first embodiment of the present invention.
Figure 8:
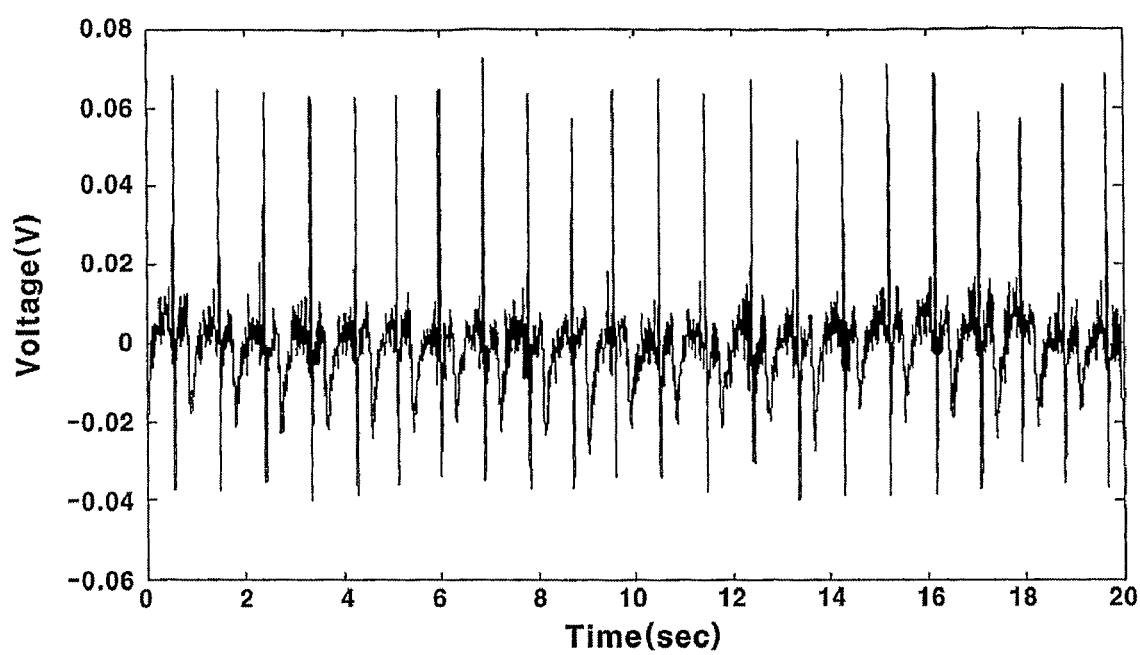
FIG. 8 is a screen illustrating ECG taking results according to the present embodiment.

FIG. 7 is a diagram illustrating an electric non-contact apparatus for taking ECGs according to a first embodiment of the present invention. FIG. 8 is a screen illustrating ECG results according to the present embodiment. FIG. 8 illustrates an example in which the electric non-contact ECG apparatus is applied to a chair that is widely used in daily life.

As illustrated in the drawing, when the electric non-contact ECG apparatus 1 according to the present invention is applied to a chair 91, at least one amplifier-attached electrode 10 is installed on at least one side of the backrest part 97 of the chair 91 on which both shoulders of the examinee are placed, the ground plate 80 is installed at a predetermined location at the seat part 99 of the chair 91 on which the buttocks of the examinee are placed, and the ECG of the examinee is taken using the taking method.

In that case where the electric non-contact ECG apparatus 1 according to the present invention is installed in the chair 91, the ground plate 80 installed in the seat part 99 of the chair 91 is used for reference voltage.

By installing the electric non-contact ECG apparatus 1 of the present invention in the chair 91 encountered in daily life, the examinee can comfortably take an ECG without being conscious of ECG taking.

In the present embodiment, the amplifier-attached electrode 10 is installed in the backrest part 97 of the chair 91 and the ground plate 80 is installed in the seat part 99 of the chair 91. However, it is possible to install at least one amplifier-attached electrode 10 on at least one side of the seat part 99 of the chair 91 on which a thigh of examinee is placed, and install the ground plate 80 in the backrest part 97 of the chair 91 on which the shoulders or back of the examinee are placed.

Meanwhile, although, in the present invention, the amplifier-attached electrode 10 and the ground plate 80 installed in the chair 91 are installed to be exposed to the outside, the amplifier-attached electrode 10 and the ground plate 80 may be embedded in the chair 91.

Furthermore, although, in the present embodiment, the amplifier-attached electrode 10 and the ground plate 80 are installed in the backrest part 97 and seat part 99 of the chair 91, respectively, the amplifier-attached electrode 10 and the ground plate 80 may be instead installed in an auxiliary backrest and an auxiliary seat, respectively, and functions as described above.

Moreover, when the amplifier-attached electrode 10 is installed in the seat part 99 of the chair 91, it may be installed at an appropriate location on the front portion of the seat part of the chair 91 that is located adjacent to or is in contact with the calf of the examinee.

As described above, the biosignal, which is passed through the input terminal of the amplifier-attached electrode 10 of the electric non-contact ECG apparatus 1 installed in the chair 91, is passed through the preamplifier 13, the high pass filter circuit 31, the band stop filter circuit 33, the amplification circuit 35 and the low pass filter circuit 37, and is displayed as a final ECG output signal on a display. That is, corresponding data is output, as is illustrated in FIG. 8.

Figure 9:
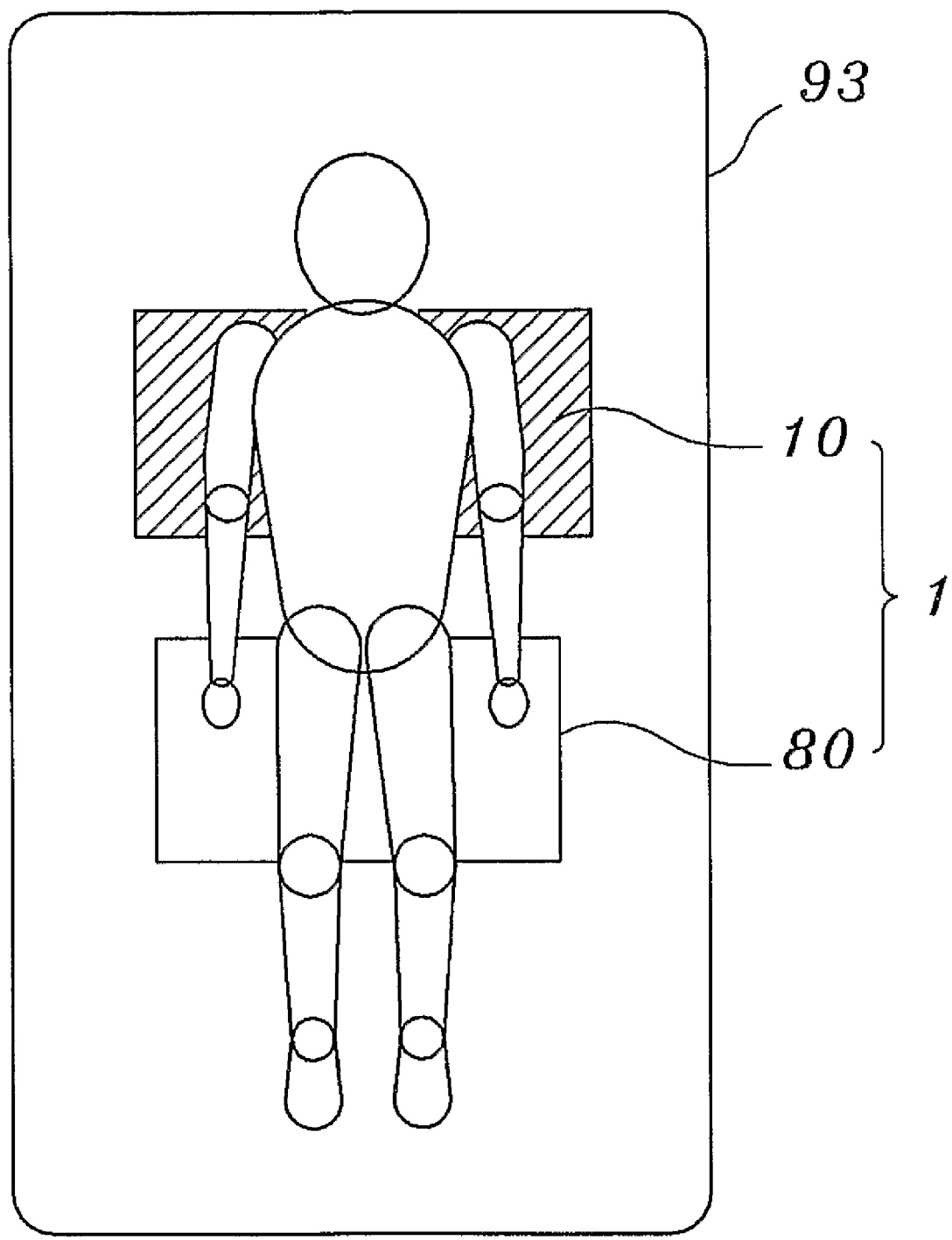
FIG. 9 is a diagram illustrating an electric non-contact apparatus for taking ECGs according to a second embodiment of the present invention.

FIG. 9 is a diagram illustrating an electric non-contact apparatus for taking ECGs according to a second embodiment of the present invention. This drawing illustrates an example in which the electric non-contact ECG apparatus is applied to a bed.

As illustrated in the drawing, when the electric non-contact ECG apparatus 1 according to the present invention is applied to a bed, at least one amplifier-attached electrode 10 is installed on one side of the upper surface of the mattress of the bed 93 where the shoulders or back of an examinee are placed, a ground plate 80 is installed on the other side of the upper surface of the mattress of the bed 93 where the buttocks of the examinee are placed, and then the examinee's ECG is taken using the above-described ECG method.

Meanwhile, when the electric non-contact ECG apparatus 1 according to the present invention is installed in the bed 93, the ground plate 80, which is installed on the other side of the upper surface of the mattress of the bed 93, is used for reference voltage.

The examinee can have an ECG taken in a comfortable state without being conscious of ECG taking by installing the electric non-contact ECG apparatus 1 of the present invention on the bed 93 on which a human can sleep.

Although, in the present embodiment, the amplifier-attached electrode 10 is installed on one side of the upper surface of the mattress of the bed 93 and the ground plate 80 is installed on the other side of the surface of the mattress of the bed 93, it is preferred that at least one amplifier-attached electrode 10 be installed on one side of the upper surface of the mattress of the bed 93, where the thigh of an examinee is placed, and the ground plate 80 be installed on the other side of the upper surface of the mattress of the bed 93, where the shoulders or back of the examinee are placed.

Meanwhile, although, in the present embodiment, the amplifier-attached electrode 10 and the ground plate 80 are installed on both sides of the upper surface of the bed 93 and exposed to the outside, it is possible to embed the amplifier-attached electrode 10 and the ground plate 80 respectively in one side and the other side of the bed 93.

Figure 10:
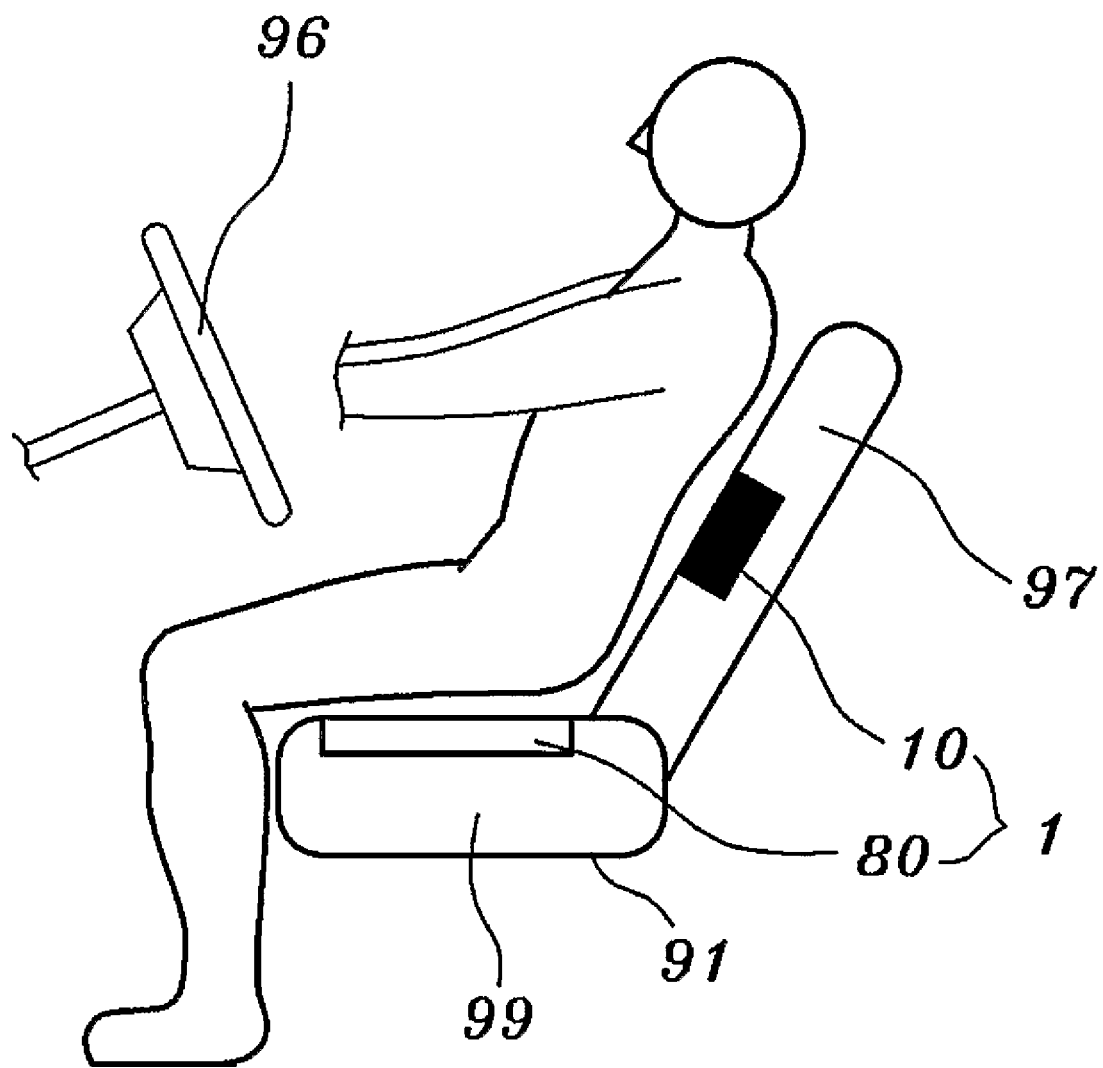
FIG. 10 is a diagram illustrating an electric non-contact apparatus for taking ECGs according to a third embodiment of the present invention.

FIG. 10 is a diagram illustrating an electric non-contact apparatus for taking ECGs according to a third embodiment of the present invention. The drawing illustrates an example in which the electric non-contact ECG apparatus is installed in the driver's seat of a vehicle.

As illustrated in the drawing, when the electric non-contact ECG apparatus 1 according to the present invention is installed in the driver's seat, one or more amplifier-attached electrodes 10 are installed at both appropriate locations on a steering wheel 96 provided in front of the driver's seat and used to steer a vehicle so that they can achieve direct contact, the ground plate 80 is installed at a predetermined location on the seat part 99 of the driver's seat 95 where the driver's buttocks are placed, and the driver's ECG is taken using the above-described method.

When the electric non-contact ECG apparatus 1 according to the present invention is installed in the driver's seat, the ground plate 80 installed in the seat part 99 of the driver's seat 95 is used for reference voltage.

Although, in the present embodiment, the amplifier-attached electrodes 10 are installed at appropriate locations on the steering wheel 96 located in front of the steering wheel 96 and the ground plate 80 is installed at a predetermined location on the seat part 99 of the driver's seat where the driver's buttocks are placed, it is preferable to install the amplifier-attached electrodes 10 on appropriate sides of the seat part 99 of the driver's seat 95, which is adjacent to or comes into contact with the thighs of the driver, and install the ground plate 80 on the steering wheel 96, which is provided in front of the driver's seat 95, is used to steer a vehicle and can come into direct contact with the driver's hands.

Meanwhile, although, in the present embodiment, the amplifier-attached electrodes 10 and the ground plate 80 are provided in the steering wheel 96 and seat part 99 of the driver's seat 95 and take the driver's ECG, it is possible to install the amplifier-attached electrodes 10 and the ground plate 80 on the backrest part 97 and seat part 99 of the driver's seat 95 and take the driver's ECG, or to embed the amplifier-attached electrodes 10 and the ground plate 80 in the backrest part 97 and seat part 99 of the driver's seat 95 and take the driver's ECG.

Meanwhile, it is possible to install amplifier-attached electrodes 10 and ground plates 80 on the seat part and backrest part of a passenger seat beside the driver and/or the seat part and backrest part of each backseat provided behind the driver's seat and the passenger seat beside the driver, and take passengers' ECGs.

The electric non-contact ECG apparatuses 1 according to the present invention are installed in the seats of a vehicle, so that the driver's and passengers' ECGs can be easily taken, and a separate alarm sound generation device is connected to the electric non-contact ECG apparatuses 1 of the present invention, so that a health-related accident, which may occur to the driver or some other passenger, and the driver's drowsy state when driving can be preemptively prevented.

Furthermore, it is desired that the electric non-contact ECG apparatus 1 according to the present invention be connected to a Global Positioning System (GPS), which is installed in a vehicle, or a communication device, such as a mobile communication terminal or a Personal Digital Assistant, which is used by the driver, via a wired or wireless connection and that the communication device be connected to a medical institution, such as a hospital, in a wireless manner, so that, when a health-related accident occurs to the driver or the passenger during the driving of a vehicle, the location of a medical institution, such as a hospital, that is closest to the current location is searched for through the GPS, the mobile communication terminal or the PDA, or a connection to a medical institution is automatically established and an emergency vehicle, such as an ambulance, is dispatched.

In the present embodiment, the electric non-contact ECG apparatus 1 installed on the driver's seat of the vehicle is connected to the GPS or the mobile communication device, such as the mobile communication terminal, in a wired or wireless connection, thus preventing a health-related accident that may occur during the driving of a vehicle. Also, it is preferable that the electric non-contact ECG apparatus 1 of the present invention installed on the chair or the bed be connected to a medical institution, such as a hospital, via a wired or wireless connection, thus preemptively preventing a health-related accident that may occur at home or the office.

Although the present invention has been illustrated and described in conjunction with the specific embodiments, those skilled in the art can easily appreciate that various modifications and variations are possible without departing from the spirit and scope of the invention as disclosed in the accompanying claims.

INDUSTRIAL APPLICABILITY

As described above, the present invention is advantageous in that the present invention is applied to a chair, a bed or a vehicle seat widely used in daily life, so that an examinee can have an electrocardiogram taken in a comfortable position, which performs the taking of the electrocardiogram on the body of a human wearing clothes without directly contacting the body, so that the examinee can unnoticeably have an electrocardiogram taken without being conscious of the taking of the electrocardiogram, thus obtaining a heart rate that can be used as a parameter useful to analyze physical and metal activities, and which does not require work of bringing the ECG apparatus and electrodes into contact with the body or work of attaching the ECG apparatus and the electrodes thereto, so that unskilled persons can use the ECG apparatus and method, thereby improving the convenience of use.

The invention claimed is:

1. An apparatus for taking ElectroCardioGrams (ECGs), the apparatus being attached to a human body, comprising:
   one or more amplifier-attached electrodes (10) installed adjacent to appropriate locations of clothes (5) without directly contacting a body (3);
   one or more filter and amplifier units (30) connected to first sides of the amplifier-attached electrodes (10) and configured to filter out external noise and amplify filtered signals;
   one or more Analog/Digital (A/D) converters (50) connected to first sides of the filter and amplifier units (30);
   a digital signal processing unit (70) provided to first sides of the A/D converter (50) and configured to transmit a taken ECG to a display and a post-processing device and the digital signal processing unit (70) comprises a subtractor (71) for obtaining a difference between the digitized biosignals input through the A/D converters (50), and a subtraction filter (73) for filtering out noise, which is generated during the subtraction, from the digital signals input through the subtractor (71); and
   a ground plate (80) installed adjacent to an appropriate location on the clothes (5) without directly contacting the body (3).

2. The apparatus as set forth in claim 1, wherein, when the electric non-contact ECG apparatus (1) is applied to a chair (91),
   the amplifier-attached electrodes (10) are installed on appropriate sides of a backrest part (97) of the chair (91) on which both shoulders of an examinee are placed, and the ground plate (80) is installed at a predetermined location on a seat part (99) of the chair (91) on which buttocks of the examinee are placed.

3. The apparatus as set forth in claim 1, wherein, when the electric non-contact ECG apparatus (1) is applied to a chair (91),
   the amplifier-attached electrodes (10) are installed on appropriate sides of a seat part (99) of the chair (91) where both thighs of an examinee are placed, and the ground plate (80) is installed at a predetermined location on a backrest part (97) of the chair (91) on which both shoulders of the examinee are placed.

4. The apparatus as set forth in claim 1, wherein, when the electric non-contact ECG apparatus (1) is applied to a bed (93), the amplifier-attached electrodes (10) are installed on a first side of an upper surface of a mattress of the bed (93) on which both shoulders of an examinee are placed, and the ground plate (80) is installed on a second side of the upper surface of the mattress of the bed (93) on which buttocks of the examinee are placed.

5. The apparatus as set forth in claim 1, wherein, when the electric non-contact ECG apparatus (1) is applied to a bed (93), the amplifier-attached electrodes (10) are installed on a first side of an upper surface of a mattress of the bed (93) on which thighs of an examinee are placed, and the ground plate (80) is installed on a second side of the upper surface of the mattress of the bed (93) on which both shoulders of the examinee are placed.

6. The apparatus as set forth in claim 1, wherein, when the electric non-contact ECG apparatus (1) is applied to a driver's seat of a vehicle, the amplifier-attached electrodes (10) are installed on appropriate sides of a steering wheel (96), which is provided in front of the driver's chair and is used to steer the vehicle, to enable direct contact, and the ground plate (80) is installed at a predetermined location on a seat part (99) of the driver's seat (95)

7. The apparatus as set forth in claim 1, wherein, when the electric non-contact ECG apparatus (1) is applied to a driver's seat of a vehicle, the amplifier-attached electrodes (10) are installed on appropriate sides of a seat part (99) of the driver's seat (95) where thighs of a driver are placed, and the ground plate (80) is installed on a steering wheel (96), which is provided in front of the driver's chair and is used to steer the vehicle, to enable direct contact.

8. A method of taking ECGs of examinees based on an ECG apparatus (1), the ECG apparatus (1) having one or more amplifier-attached electrodes (10), one or more filter and amplifier units (30), one or more A/D converters (50), a digital signal processing unit (70) and a ground plate (80), comprising:

the step (S1) at which biosignals, which are generated in an examiner's body (3), are input to the amplifier-attached electrodes (10) across worn clothes (5) via displacement current;

the step (S2) at which the input biosignals are amplified and impedance-converted by the amplifier-attached electrodes (10);

the step (S3) at which the biosignals, which are converted by the amplifier-attached electrodes (10), are input to the filter and amplifier units (30);

the step (S4) at which the input biosignals are filtered and amplified by the filter and amplifier units (30);

the step (S5) at which biosignal-based analog signals, which are output from the filter and amplifier units (30), are input to the A/D converters (50);

the step (S6) at which the biosignal-based analog signals are converted into digital signals by the A/D converters (50);

the step (S7) at which the digital signals, which are obtained by the A/D converters (50), are input to the digital signal processing unit (70), and the digital signals are subtracted by the subtractor (71), and noise, which is generated during the subtraction through the subtractor (71), is eliminated by a subtraction filter (73); and the step (S8) at which an ECG, on which subtraction and filtering are performed by the digital signal processing unit (70), is displayed on a display.

9. A method of taking ECGs of examinees based on an ECG apparatus (1), the ECG apparatus (1) having one or more amplifier-attached electrodes (10), one or more filter and amplifier units (30), one or more A/D converters (50), a digital signal processing unit (70) and a ground plate (80), comprising:

the step (S1) at which biosignals, which are generated in an examiner's body (3), are input to the amplifier-attached electrodes (10) across worn clothes (5) via displacement current; the step (S2) at which the input biosignals are amplified and impedance-converted by the amplifier-attached electrodes (10) and the ground plate (80) eliminates common-mode noise of the body in such a way as to detect the common-mode noise by performing subtraction and addition on the signals input from the amplifier-attached electrodes (10), and connect to the amplifier-attached electrodes (10) in a negative feedback fashion;

the step (S3) at which the biosignals, which are converted by the amplifier-attached electrodes (10), are input to the filter and amplifier units (30);

the step (S4) at which the input biosignals are filtered and amplified by the filter and amplifier units (30);

the step (S5) at which biosignal-based analog signals, which are output from the filter and amplifier units (30), are input to the A/D converters (50);

the step (S6) at which the biosignal-based analog signals are converted into digital signals by the A/D converters (50);

the step (S7) at which the digital signals, which are obtained by the A/D converters (50), are input to the digital signal processing unit (70); and the step (S8) at which an ECG, on which subtraction and filtering are performed by the digital signal processing unit (70), is displayed on a display.

* * * * *

UNITED STATES PATENT AND TRADEMARK OFFICE
CERTIFICATE OF CORRECTION

PATENT NO.        : 7,684,854 B2                          Page 1 of 1
APPLICATION NO.   : 11/631704
DATED             : March 23, 2010
INVENTOR(S)       : Kwang-Suk Park et al.

It is certified that error appears in the above-identified patent and that said Letters Patent is hereby corrected as shown below:

In Column 12, line 41, claim 1, delete "substraction" and insert --subtraction--.

Signed and Sealed this

Eleventh Day of May, 2010

David J. Kappos
*Director of the United States Patent and Trademark Office*